US006988393B2

United States Patent
Feustel

(10) Patent No.: US 6,988,393 B2
(45) Date of Patent: Jan. 24, 2006

(54) APPARATUS FOR DETERMINING RHEOLOGICAL PROPERTIES

(76) Inventor: Manfred Feustel, Koenigsforstrstrasse 56 C, Cologne (DE), 51109

( * ) Notice: Subject to any disclaimer, the term of this patent is extended or adjusted under 35 U.S.C. 154(b) by 0 days.

(21) Appl. No.: 10/784,883

(22) Filed: Feb. 24, 2004

(65) Prior Publication Data

US 2004/0226349 A1 Nov. 18, 2004

Related U.S. Application Data

(63) Continuation of application No. PCT/DE02/03119, filed on Aug. 23, 2002.

(30) Foreign Application Priority Data

Aug. 24, 2001 (DE) .......................... 101 40 711

(51) Int. Cl.
*G01N 11/10* (2006.01)

(52) U.S. Cl. ..................................... 73/54.39; 356/427
(58) Field of Classification Search ................ 73/54.02, 73/54.37, 54.39; 356/426, 427
See application file for complete search history.

(56) References Cited

U.S. PATENT DOCUMENTS

| | | | | |
|---|---|---|---|---|
| 4,435,080 A | * | 3/1984 | Maly et al. | ................... 356/426 |
| 4,936,674 A | * | 6/1990 | Ikeda et al. | ................... 356/39 |
| 5,105,655 A | * | 4/1992 | Khan et al. | ................ 73/54.39 |
| 5,905,196 A | | 5/1999 | Parshall | |
| 6,167,752 B1 | | 1/2001 | Gerhard | |

FOREIGN PATENT DOCUMENTS

DE 68919356 3/1995

OTHER PUBLICATIONS

Skytt, M. et al., "A New Rheometer Measuring Infrared Dichroism in Molten Polymers Subjected to Transient and Steady Shear Flow" Polymer Engineering & Science, Society of Plastics Engineers, U.S. vol. 36, No. 13, Jul. 15, 1996, pp 1737–1744.

Matsuzaka et al., "A Rheo–Optical Apparatus for Simultaneous Detection of Rheology, Small–Angle Light Scattering, and Optical Microscopy Under Transient, Oscillatory, and Continuous Shear Flows" Review of Scientific Instruments, American Institute of Physics, New York, U.S., vol.. 70, No. 5, May 1999, pp 2387–2397.

* cited by examiner

*Primary Examiner*—Michael Cygan
(74) *Attorney, Agent, or Firm*—Crowell & Moring LLP

(57) ABSTRACT

An apparatus (1) including two plates (3, 4) which can be rotated in relation to each other and between which the rheological properties of a test substance (6) disposed in an intervening area (5) can be determined. At least one of the plates (3) is provided with a light inlet (2) sealed by a body (8, 10) in order to carry out an optical measurement method, e.g., infrared spectroscopy, enabling other characteristics of the test substance to be determined simultaneously. The body (8, 10) is light permeable at least in the infrared spectrum, and on its side facing the intervening area (5), the body (8, 10) terminates in a flush contour relative to the to the plate (3) in which it is provided so that undesirable interactions which might affect the measurement of the rheological properties of the test substance (6) are reliably excluded.

20 Claims, 1 Drawing Sheet

APPARATUS FOR DETERMINING RHEOLOGICAL PROPERTIES

CROSS REFERENCE TO RELATED APPLICATIONS

This application is a continuation of international patent application no. PCT/DE02/03119, filed Aug. 23, 2002 designating the United States of America, and published in German as WO 03/019152, the entire disclosure of which is incorporated herein by reference. Priority is claimed based on Federal Republic of Germany patent application no. DE 101 40 711.4, filed Aug. 24, 2001.

BACKGROUND OF THE INVENTION

The invention relates to an apparatus with two plates, which are spaced apart from each other and are movable in relation to each other and which define an intervening space for receiving a substance to be tested, whose rheological, particularly viscometric, properties can be determined simultaneously with another measurement procedure that can be carried out by the apparatus.

An apparatus of this general type is disclosed, for example, in published European patent application no. EP 750,186 in which the rheological properties of a substance are determined between two plates. For this purpose, the bottom plate of two substantially parallel plates is driven and set into rotation. As a result, the substance is subjected to stress, particularly shear stress, and a sensor forwards a signal to a control unit. At the same time, heat is applied to the substance and an additional sensor is used to determine thermal characteristics.

Carrying out the two measurement procedures simultaneously has two essential advantages compared to carrying out two separate measurement procedures. On the one hand, the two procedures can be carried out simultaneously on the same sample so as to exclude possible error influences due to non-homogeneities in the substance. Furthermore, any possible changes that the substance may undergo in the interim when the two measurement procedures are carried out can also be avoided. On the other hand, the two measurement procedures can be subjected to a comparative evaluation, so that the measured data can be checked. This makes it possible to detect any interfering environmental influences, which are then excluded from consideration in the further analysis.

The two measurement methods are not simply modifications of the same measurement principle but provide insights into the properties of the substance by independent routes. The corresponding information, however, makes it possible to draw conclusions about the results of the respectively other measurement method.

However, in carrying out such rheological tests, the high demands placed on the surface quality of the plates are problematic. As a result, it is not possible, for example, to arrange sensors in the intervening space between the plates or on the surface of the plates, because even the slightest changes in the surface quality can lead to errors in the rheological test.

It is also know to use optical spectroscopic measurement methods for testing substances. The substance is measured either in transmission or in directional or diffuse reflection. While specific conditions have to be met for measurement methods using the reflection principle, transmission measurements, particularly in infrared spectroscopy, require a time-consuming preparation of the substance. For example, complicated microtome sections or molten films have to be prepared for this purpose.

In contrast, a measurement method based on the principle of attenuated total reflection (ATR) offers an almost universal means for rapidly and simply analyzing a wide variety of substances. The ATR method is based on substance-specific infrared absorption at the interface between a medium with a high refractive index and the substance, which has a relatively low refractive index. For this purpose it is sufficient to provide adequate contact between the substance and the ATR element. The principle of ATR is based on injecting an infrared beam into a crystal material that is transparent to infrared light and whose refractive index is greater than the refractive index of the substance. On its path through the ATR element, the infrared beam is totally reflected one or more times. At the points where the beam contacts the interface between the ATR element and the substance, substance-specific portions of the infrared beam are absorbed. This produces a spectrum that is very similar to transmission. The ratio between the total reflection and the attenuated values is determined as a function of the transmission across the wavelength of the infrared radiation. One advantage compared to transmission measurement methods is that the layer thickness of the substance is irrelevant in the ATR method. Because of its enormous advantages regarding substance preparation, the ATR technique, today, has largely replaced the transmission methods.

U.S. Pat. No. 5,905,196 A discloses a viscometer based on the principle of the emission method. The rheological stress of the sample generates friction heat, and the corresponding thermal radiation is measured without contact and without influencing the measurement process itself. For this purpose a window is provided. A necessary condition for carrying out this method is that the infrared thermal radiation is not influenced, i.e., particularly not attenuated, as it passes through the window. As a result, the window has to be highly transparent.

The German publication DE 689 19 256 T2 discloses a transmission method in which the light beam passes through the substance parallel to the lower plate or the upper cone. The transmission path thus corresponds approximately to the diameter of the cone-plate arrangement. A drawback is that the described arrangement results in a comparatively long transmission path, which substantially limits the selection of the wavelength range of the light.

SUMMARY OF THE INVENTION

The object of the invention is to provide an apparatus for determining not only the rheological properties of a substance but also other properties of the substance using an additional measurement method without any influence or effect on the rheological measurement results.

This and other objects are achieved in accordance with the present invention by providing an apparatus for determining rheological properties of a test substance, the apparatus comprising two plates which are spaced apart from each other and are movable relative to each other and which delimit an intervening space for receiving the test substance, the apparatus further comprising a light passage that does not alter the intervening space, the light passage facilitating optical measurement of the test substance, whereby an optical analysis of the test substance can be carried out simultaneously with the determination of rheological properties.

Further advantageous embodiments and preferred features of the invention are described hereinafter.

Thus, the invention provides an apparatus in which the device for carrying out an optical, particularly an infrared spectroscopic measurement method has a light passage that does not change the intervening space. This makes it possible to carry out the determination of the rheological properties simultaneously with the infrared spectroscopy, without the risk of an interaction between the two measurement methods. In particular, a direct contact between the substance and a sensor is avoided, such that any reactions on the surface of the plates are excluded.

A particularly advantageous embodiment of the invention is achieved if the light passage is formed by a segment transmissive to infrared light whose contour terminates flush with a surface of the plate oriented facing the intervening space. As a result, the infrared light required for infrared spectroscopy can be applied to the substance through the plate, so that the intervening space, in particular, can be sealed on all sides. At the same time, the light passage can be arranged specifically in the positions that are subjected to stress for carrying out the rheological test and, therefore, have particular significance and informative value for the review by means of the spectroscopic measurement method. Due to the flush termination of the contour or surface of the segment, reactions of the segment on the rheological measured values are excluded.

A particularly practical modification of the invention is obtained if the light passage is provided with a transmissive body of great hardness. As a result, even continuous stress on a surface of the transmissive body that is inclined toward the substance does not affect the measured rheological values. The apparatus can thus be operated practically without wear, and the accuracy and comparability of the obtained measurement results can be significantly improved. In practice, diamond, ZnSe or germaniumf have proven particularly suitable. In particular, the body has a higher refractive index compared to the substance to be tested.

A further, particularly advantageous modification is obtained if the body has a light-introduction surface on a segment opposite the intervening space. This light-introduction surface is sloped in relation to the plane of the plate according to the desired light entry angle. As a result, the losses due to retro-reflection that occur on the light-introduction surface are only minor. This further improves the measurement accuracy.

Another particularly practical embodiment of the invention is obtained if the apparatus, in addition to the first light passage, has a second light passage on the same plate. The infrared light beam is injected into the substance through the first light passage and then exits through the second light passage, such that it can be detected by an external sensor. In particular, the first and the second light passage are arranged on the same plate and are sealed by a common, or each by a separate, transmissive body with flush contours.

It is particularly advantageous if the second plate has a reflective surface from which the infrared light beam entering the intervening space through the light passage is reflected.

Another particularly advantageous modification of the present invention is attained if at least one of the plates can be heated or cooled in order to obtain a desired temperature. This makes it possible to prevent undesirable thermal influences on the test substance. In particular, the measurement results can be uniformly related to a predefined temperature.

Another particularly practical embodiment is furthermore achieved if one of the plates is made at least partially conical to further improve the informative value of the rheological measurement results. For this purpose, the plate can, for example, be interchangeable or it can have a holding fixture for an add-on element.

A further particularly practical embodiment in which the plates have an adjustable distance between them ensures that both the reflection measurement method and the attenuated total reflection spectroscopic technique can be used. This makes it possible to select the method that is best suited for a given substance.

In a simple embodiment, the second plate can be driven while the first plate is stationary to induce the stresses necessary for the rheological test.

The apparatus is suitable for carrying out different infrared spectroscopic methods. Particularly promising, however, is an embodiment in which the second measurement method is configured as an ATR method, which can be carried out by the apparatus. This substantially reduces the time-consuming preparation of the substance, so that the measurement method can be carried out at low cost. As a result, the apparatus is suitable for testing extremely small layer thicknesses of the substance. The external dimensions of the substance do not affect the measurement.

For this purpose, another embodiment is particularly suitable, in which the body has several reflective surfaces. This produces several infrared light entry surfaces into the substance, such that the measurement result and the informative value of the determined spectrum is further improved.

In another particularly practical embodiment of the invention, the apparatus can optionally be used to carry out the ATR measurement method or another infrared spectroscopic measurement method, making it possible to individually select the measurement method that is best suited for the specific case. The same light passage can be used to enable a simple construction of the apparatus.

It is furthermore particularly promising if the apparatus has a control unit for the recording and the comparative evaluation of the measured values determined by means of the rheological measurement method and the spectroscopic measurement method. This makes it possible to relate the measured values obtained via independent measurement methods in order to filter out, for example, undesirable external influences.

The values obtained by means of the measurement methods can be used to detect undesirable external influences, which are then excluded from the further analysis. Particularly advantageous is an embodiment in which the control unit can be used to derive a viscosity value based on known substances. As a result, the infrared spectroscopic method is used not only for plausibility checks but also to determine rheological characteristics through interpolation or extrapolation of known values for the respective substance, enabling a direct verification of the different measured values.

BRIEF DESCRIPTION OF THE DRAWINGS

The invention will be described in further detail hereinafter with reference to illustrative preferred embodiments shown in the accompanying drawing figures, in which.

DETAILED DESCRIPTION OF PREFERRED EMBODIMENTS

Figure 1:
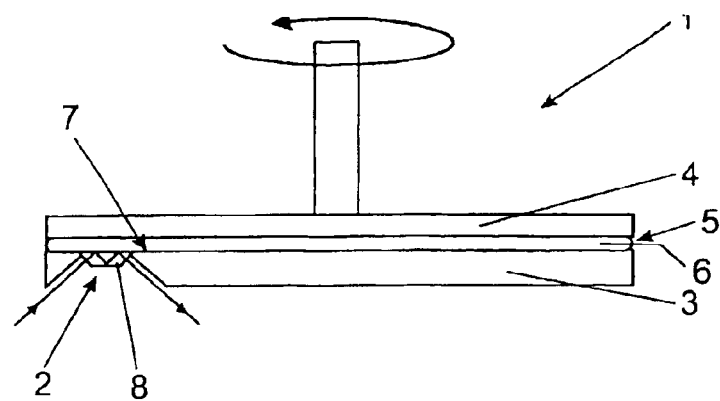
FIG. 1 shows an apparatus according to the invention with a light passage for carrying out an infrared spectroscopic measurement method based on the principle of attenuated total reflection.

FIG. 1 shows an apparatus 1 according to the invention with a light passage 2 for infrared light to carry out an infrared spectroscopic measurement method based on the principle of attenuated total reflection. The light passage 2 is arranged on a first plate 3, which together with a second plate 4, rotatable relative to the first plate 3, encloses an intervening space 5. This intervening space 5 serves to accommodate a substance 6 to be tested. For this purpose the substance is subjected to stress by the plates 3, 4. The determined rheological properties and the results of the infrared spectroscopic measurement are then compared. To prevent any undesirable mutual influence during the simultaneous testing, a transmissive body 8, e.g., a diamond, whose contour ends flush with a surface 7 of the plate 3, is used to seal the light passage 2. As a result the apparatus 1 is very durable and almost wear-free. Depending on the size of the body 8, one or more internal reflections can occur at the interface between the body 8 and the substance 6.

Figure 2:
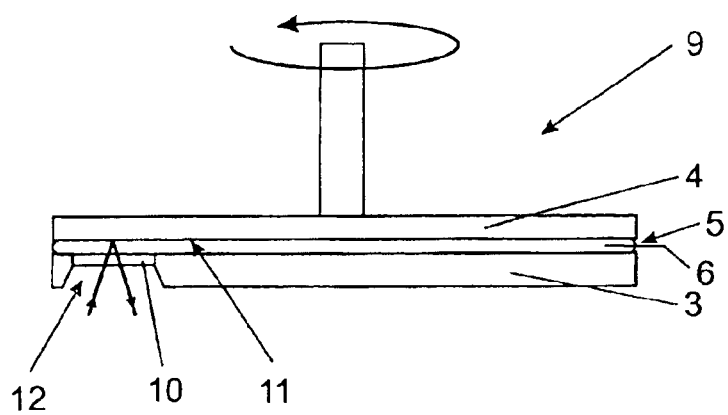
FIG. 2 shows another apparatus for carrying out a measurement method involving reflection.

In the apparatus 9 shown in FIG. 2, the first plate 3 is sealed with a body 10 through which the infrared light required for reflection spectroscopy reaches the intervening space 5 at a steeper angle. The desired reflection of the infrared light thus occurs after the light has penetrated the substance 6 on a reflection surface 11 of the second plate 4 on which the infrared light is reflected in the direction of a light passage 12. The reflection spectrum thus produced is detected by a sensor (not shown) and is supplied to a control unit as a supplement to and for comparative evaluation of the rheological test. The light passage 12 can have any geometric shape.

Figure 3:
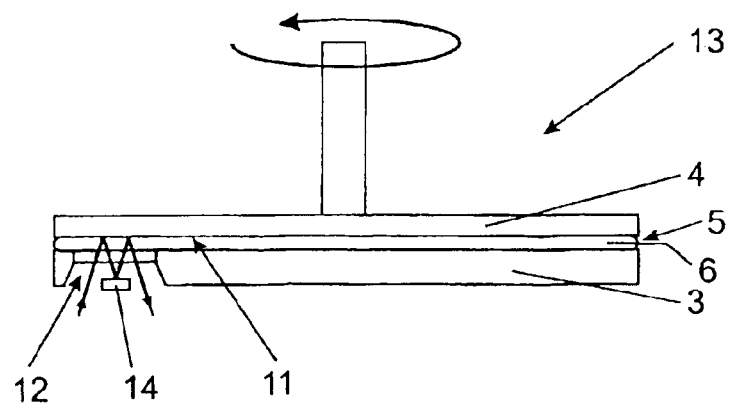
FIG. 3 shows a modification of the apparatus of FIG. 2 with an additional mirror.

The apparatus 13 shown in FIG. 3 is slightly modified. Here, the infrared light is reflected from the reflection surface 11 of the plate 4 after passing through the substance 6 onto an additional mirror 14 back in the direction of the reflection surface 11. The infrared light thus passes through the substance 6 four times before it exits from the intervening space 5 through the light passage 12 in the plate 3. This provides an additional transmission spectrum, which optimally supplements the existing measured values.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. An apparatus for determining rheological properties of a test substance, said apparatus comprising two plates which are spaced apart from each other and are movable relative to each other and which delimit an intervening space for receiving the test substance, said apparatus further comprising a light passage that does not alter said intervening space, said light passage facilitating optical measurement of the test substance, whereby an optical analysis of the test substance can be carried out simultaneously with the determination of rheological properties, wherein the light passage comprises a light transmissive body having a light-introduction surface on a segment opposite the intervening space, said light-introduction surface being inclined in accordance with a desired light entry angle relative to the plane of the plate.

2. An apparatus according to claim 1, wherein said apparatus is adapted to determine the viscosimetric properties of the test substance.

3. An apparatus according to claim 1, wherein said optical measurement is a spectroscopic analysis.

4. An apparatus according to claim 1, wherein said spectroscopic analysis is an infrared spectroscopic analysis.

5. An apparatus according to claim 1, wherein the light passage is formed by a segment transmissive to infrared light and having a contour which terminates flush with a surface of a plate that is oriented facing the intervening space.

6. An apparatus according to claim 1, wherein the light transmissive body is selected from the group consisting of diamond, ZnSe and germanium.

7. An apparatus according to claim 1, wherein the apparatus further comprises a second light passage on the same plate as the first light passage.

8. An apparatus according to claim 1, wherein at least one of the plates comprises means for heating or cooling in order to obtain a desired temperature.

9. An apparatus according to claim 1, wherein one of the plates is at least partially conical.

10. An apparatus according to claim 1, wherein the plates are spaced apart from each other by an adjustable distance.

11. An apparatus according to claim 1, wherein the second plate is movably driven.

12. An apparatus according to claim 1, wherein the apparatus can be selectively used to carry out an attenuated total reflection (ATR) measurement or an infrared spectroscopic measurement.

13. An apparatus according to claim 1, wherein the apparatus includes a control unit for recording measured values obtained by the rheological measurement and the optical measurement and evaluating the measured values by comparison to reference values.

14. An apparatus according to claim 13, wherein said reference values represent viscosity values of known substances.

15. An apparatus according to claim 1, wherein said two plates are rotatable relative to each other.

16. An apparatus according to claim 1, wherein the second plate has a reflection surface positioned to reflect a light beam entering the intervening space through the light passage.

17. An apparatus for determining rheological properties of a test substance, said apparatus comprising two plates which are spaced apart from each other and are movable relative to each other and which delimit an intervening space for receiving the test substance, said apparatus further comprising a light passage that does not alter said intervening space, said light passage facilitating optical measurement of the test substance, whereby an optical analysis of the test substance can be carried out simultaneously with the determination of rheological properties, wherein the second plate has a reflection surface positioned to reflect a light beam entering the intervening space through the light passage.

18. An apparatus according to claim 17, wherein said reflection surface is an infrared reflective surface, and said light be is an infrared beam.

19. An apparatus for determining rheological properties of a test substance, said apparatus comprising two plates which are spaced apart from each other and are movable relative to each other and which delimit an intervening space for receiving the test substance, said apparatus further comprising a light passage that does not alter said intervening space, said light passage facilitating optical measurement of the test substance, whereby an optical analysis of the test substance can be carried out simultaneously with the determination of rheological properties, wherein the optical measurement is an attenuated total reflection (ATR) measurement that can be carried out by the apparatus.

20. An apparatus for determining rheological properties of a test substance, said apparatus comprising two plates which are spaced apart from each other and are movable relative to each other and which delimit an intervening space for receiving the test substance, said apparatus further comprising a light passage that does not alter said intervening space, said light passage facilitating optical measurement of the test substance, whereby an optical analysis of the test substance can be carried out simultaneously with the determination of rheological properties, wherein the light passage comprises a light transmissive body with a plurality of light reflection surfaces.

* * * * *